(12) United States Patent
Carlson et al.

(10) Patent No.: US 10,765,869 B2
(45) Date of Patent: Sep. 8, 2020

(54) PRECISION DELIVERY OF ELECTRICAL STIMULATION

(71) Applicant: Medtronic, Inc., Minneapolis, MN (US)

(72) Inventors: David L. Carlson, Fridley, MN (US); Heather D. Orser, Farmington, MN (US); Dale G. Suilmann, Elk River, MN (US); Kenneth J. Gutzman, Lino Lakes, MN (US); Gregory J. Loxtercamp, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 379 days.

(21) Appl. No.: 15/848,291

(22) Filed: Dec. 20, 2017

(65) Prior Publication Data

US 2018/0200523 A1 Jul. 19, 2018

Related U.S. Application Data

(60) Provisional application No. 62/445,996, filed on Jan. 13, 2017.

(51) Int. Cl.
*A61N 1/36* (2006.01)
*A61N 1/372* (2006.01)
(Continued)

(52) U.S. Cl.
CPC ............ *A61N 1/36167* (2013.01); *A61B 5/04* (2013.01); *A61B 5/0478* (2013.01); *A61N 1/0534* (2013.01); *A61N 1/08* (2013.01); *A61N 1/36132* (2013.01); *A61N 1/36139* (2013.01); *A61N 1/37211* (2013.01); *A61N 1/37264* (2013.01); *A61N 1/37288* (2013.01);
(Continued)

(58) Field of Classification Search
CPC .......................... A61N 1/36167; A61N 1/0534
USPC .......................................................... 607/2
See application file for complete search history.

(56) References Cited

U.S. PATENT DOCUMENTS 5,607,459 A 3/1997 Paul et al.
8,280,516 B2 10/2012 Graupe
(Continued)

OTHER PUBLICATIONS

International Search Report and Written Opinion of International Application No. PCT/US2017/067862, dated Mar. 9, 2018, 16 pp.
(Continued)

*Primary Examiner* — Nadia A Mahmood
(74) *Attorney, Agent, or Firm* — Shumaker & Sieffert, P.A.

(57) ABSTRACT

An example method for controlling delivery of electrical stimulation therapy includes maintaining, by one or more processors of a medical device configured to deliver electrical stimulation to a patient, a counter tied to a clock used by the medical device to deliver the electrical stimulation to the patient; and obtaining, by the one or more processors, one or more representations of sensed electrical signals for the patient that are referenced to counts of the counter. In this example, the method also includes identifying, based on the one or more representations of the sensed electrical signals for the patient, a count of the counter at which stimulation is to be delivered to the patient; and delivering, by the medical device and to the patient, electrical stimulation based on the identified count of the counter.

26 Claims, 7 Drawing Sheets

(51) Int. Cl.
*A61N 1/05* (2006.01)
*A61B 5/04* (2006.01)
*A61B 5/0478* (2006.01)
*A61N 1/08* (2006.01)
*A61B 5/00* (2006.01)

(52) U.S. Cl.
CPC .......... *A61B 5/7275* (2013.01); *A61B 5/7282* (2013.01); *A61B 5/7285* (2013.01); *A61N 1/0551* (2013.01); *A61N 1/3616* (2013.01)

(56) References Cited

U.S. PATENT DOCUMENTS

| | | |
|---|---|---|
| 8,688,222 B2 | 4/2014 | Smith |
| 2009/0275811 A1 | 11/2009 | Schatz et al. |
| 2010/0076525 A1 | 3/2010 | Skelton et al. |
| 2010/0094377 A1 | 4/2010 | Graupe |
| 2010/0106217 A1 | 4/2010 | Colborn |
| 2010/0114200 A1 | 5/2010 | Krause et al. |
| 2011/0190850 A1 | 8/2011 | Reinke et al. |
| 2014/0066796 A1 | 3/2014 | Davis et al. |
| 2015/0012057 A1 | 1/2015 | Carlson et al. |
| 2016/0144190 A1* | 5/2016 | Cao ..................... A61B 5/0456 607/17 |

OTHER PUBLICATIONS

International Preliminary Report on Patentability from International Application No. PCT/US2017/067862, dated Jul. 25, 2019, 9 pp.

* cited by examiner

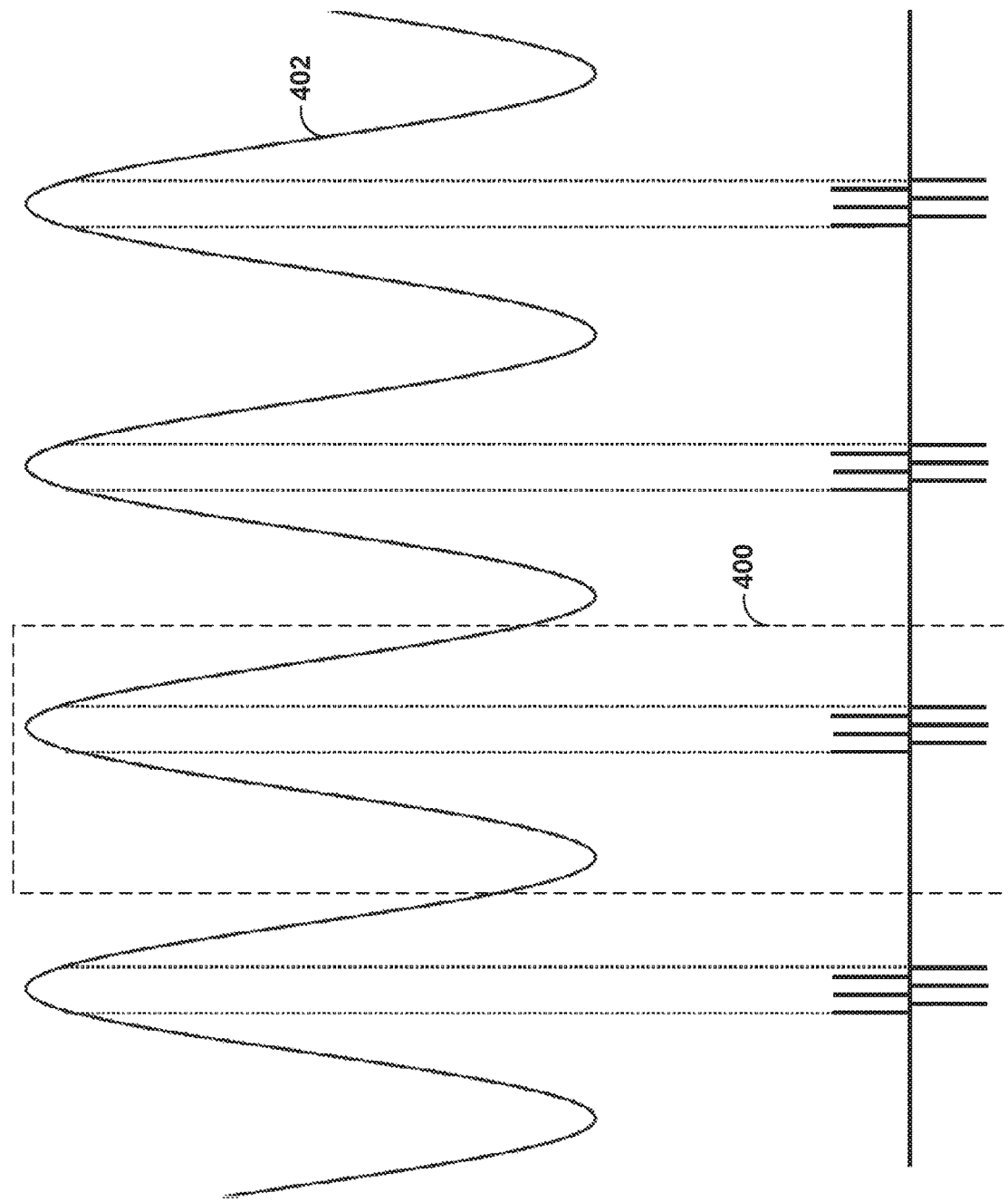

PRECISION DELIVERY OF ELECTRICAL STIMULATION

CROSS-REFERENCE TO RELATED APPLICATIONS

This application claims the benefit of U.S. Provisional Application Ser. No. 62/445,996 filed on Jan. 13, 2017 and herein incorporated by reference in its entirety.

GOVERNMENT INTEREST

This invention was made with government interest under prime award number N66001-14-2-4-31, sub-award number 56400 awarded by DARPA. The government has certain rights in the invention.

TECHNICAL FIELD

The disclosure relates to electrical stimulation therapy.

BACKGROUND

Implantable medical devices, such as electrical stimulators or therapeutic agent delivery devices, have been proposed for use in different therapeutic applications, such as deep brain stimulation (DBS), spinal cord stimulation (SCS), pelvic stimulation, gastric stimulation, peripheral nerve stimulation, functional electrical stimulation or delivery of pharmaceutical agents, insulin, pain relieving agents or anti-inflammatory agents to a target tissue site within a patient. In some therapy systems, an implantable electrical stimulator delivers electrical therapy to a target tissue site within a patient with the aid of one or more electrodes, which may be deployed by medical leads and/or on a housing of the electrical stimulator, or both.

During a programming session, which may occur during implant of the medical device, during a trial session, or during an in-clinic or remote follow-up session after the medical device is implanted in the patient, a clinician may generate one or more therapy programs (also referred to as therapy parameter sets) that are found to provide efficacious therapy to the patient, where each therapy program may define values for a set of therapy parameters. A medical device may deliver therapy to a patient according to one or more stored therapy programs. In the case of electrical stimulation, the therapy parameters may define characteristics of the electrical stimulation waveform to be delivered. In examples in which electrical stimulation is delivered in the form of electrical pulses, for example, the therapy parameters may include an electrode configuration including an electrode combination and electrode polarities, an amplitude, which may be a current or voltage amplitude, a pulse width, and a pulse rate.

Some medical devices are configured to sense a patient parameter, such as a bioelectrical brain signal. A sensed patient parameter may be used for various purposes, such as to control therapy delivery by a medical device.

SUMMARY

In one example, a method for controlling delivery of electrical stimulation therapy includes maintaining, by one or more processors of a medical device configured to deliver electrical stimulation to a patient, a counter tied to a clock used by the medical device to deliver the electrical stimulation to the patient; obtaining, by the one or more processors, one or more representations of sensed electrical signals for the patient that are referenced to counts of the counter; identifying, by the one or more processors and based on the one or more representations of the sensed electrical signals for the patient, a count of the counter at which stimulation is to be delivered to the patient; and delivering, by the medical device and to the patient, electrical stimulation based on the identified count of the counter.

In another example, a medical device includes a memory configured to store a representation of sensed electrical signals for a patient; and one or more processors. In this example, the one or more processors are configured to: maintain a counter tied to a clock used by the medical device to deliver electrical stimulation to a patient; obtain one or more representations of sensed electrical signals for the patient that are referenced to counts of the counter; identify, based on the one or more representations of the sensed electrical signals for the patient, a count of the counter at which stimulation is to be delivered to the patient; and deliver, to the patient, electrical stimulation based on the identified count of the counter.

In another example, a computer-readable storage medium storing instructions that, when executed, cause one or more processors of a medical device to: maintain a counter tied to a clock used by the medical device to deliver electrical stimulation to a patient; obtain one or more representations of sensed electrical signals for the patient that are referenced to counts of the counter; identify, based on the one or more representations of the sensed electrical signals for the patient, a count of the counter at which stimulation is to be delivered to the patient; and deliver, to the patient, electrical stimulation based on the identified count of the counter.

In another example, a medical device includes means for maintaining a counter tied to a clock used by the medical device to deliver the electrical stimulation to the patient; means for obtaining one or more representations of sensed electrical signals for the patient that are referenced to counts of the counter; means for identifying, based on the one or more representations of the sensed electrical signals for the patient, a count of the counter at which stimulation is to be delivered to the patient; and means for delivering, to the patient, electrical stimulation based on the identified count of the counter.

In another example, a method for controlling delivery of electrical stimulation therapy include receiving, by a telemetry module of a device and from a medical device that maintains a counter tied to a clock used by the medical device to deliver the electrical stimulation to a patient, one or more representations of sensed electrical signals for the patient that are referenced to counts of the counter; identify, by one or more processors of the device and based the representations of sensed electrical signals for the patient, a count of the counter at which stimulation is to be delivered to the patient; and output, by the telemetry module and to the medical device, a command to deliver stimulation based on the identified count of the counter.

In another example, a medical device programmer includes a telemetry module configured to communicate with a medical device that maintains a counter tied to a clock used by the medical device to deliver the electrical stimulation to a patient; and one or more processors. In this example, the one or more processors are configured to: receive, via the telemetry module from the medical device, one or more representations of sensed electrical signals for the patient that are referenced to counts of the counter; identify, based the representations of sensed electrical signals for the patient, a count of the counter at which stimulation is to be delivered to the patient; and output, via the telemetry module and to the medical device, a command to deliver stimulation based on the identified count of the counter.

In another example, a computer-readable storage medium storing instructions that, when executed, cause one or more processors of a medical device programmer to: receive, via a telemetry module of the medical device programmer and from a medical device that maintains a counter tied to a clock used by the medical device to deliver the electrical stimulation to a patient, one or more representations of sensed electrical signals for the patient that are referenced to counts of the counter; identify, based the representations of sensed electrical signals for the patient, a count of the counter at which stimulation is to be delivered to the patient; and output, via the telemetry module and to the medical device, a command to deliver stimulation based on the identified count of the counter.

In another example, a medical device programmer includes means for receiving, from a medical device that maintains a counter tied to a clock used by the medical device to deliver the electrical stimulation to a patient, one or more representations of sensed electrical signals for the patient that are referenced to counts of the counter; means for identifying, based the representations of sensed electrical signals for the patient, a count of the counter at which stimulation is to be delivered to the patient; and means for outputting, to the medical device, a command to deliver stimulation based on the identified count of the counter.

In another example, a system includes a medical device configured to maintain a counter tied to a clock used by the medical device to deliver the electrical stimulation to the patient; and one or more processors configured to identify, based on one or more representations of sensed electrical signals for the patient that are referenced to counts of the counter, a count of the counter at which stimulation is to be delivered to the patient. In this example, the medical device is configured to deliver stimulation to the patient based on the identified count.

The details of one or more examples are set forth in the accompanying drawings and the description below. Other features, objects, and advantages of the disclosure will be apparent from the description and drawings, and from the claims.

BRIEF DESCRIPTION OF DRAWINGS

FIGS. 4A and 4B are graphs illustrating example delivery of electrical stimulation therapy.

DETAILED DESCRIPTION

Figure 1:
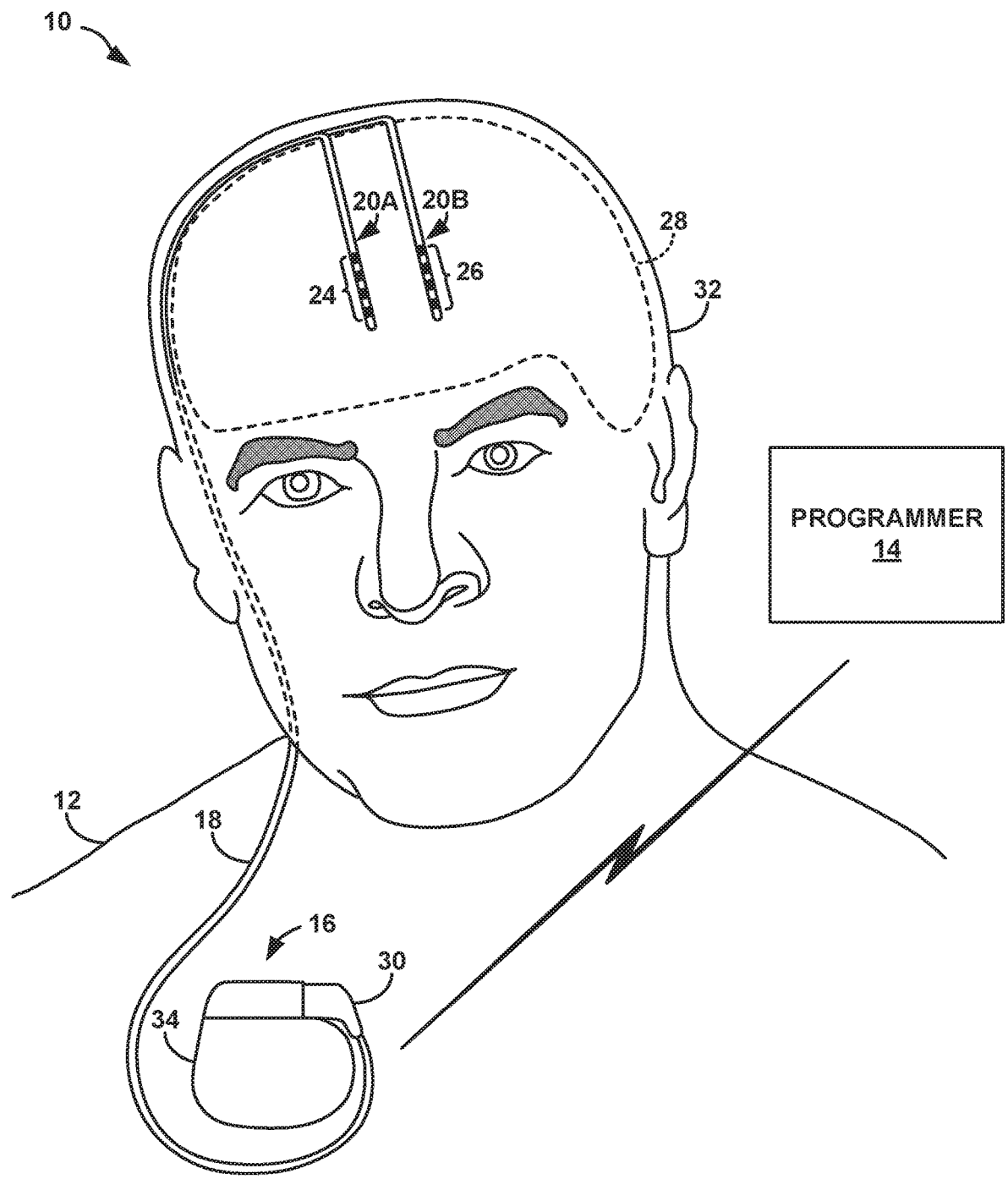
FIG. 1 is a conceptual diagram illustrating an example deep brain stimulation (DBS) system configured to deliver electrical stimulation therapy to a tissue site within a brain of a patient.

In general, the disclosure is directed to devices, systems, and methods for delivering electrical stimulation to a patient at a precise time. A device may deliver electrical stimulation to a patient using open-loop or closed-loop techniques. In either case, responsive to determining that stimulation is to be delivered, the device may generate and deliver the electrical stimulation. In some examples, the device may immediately deliver the electrical stimulation. However, in some examples, it may be desirable for the device to deliver the electrical stimulation at a precise time in the future. For instance, it may be desirable for the device to synchronize delivery of the electrical stimulation with activity of the patient (e.g., peak tremor from an external source and/or electrical activity of the patient's brain). However, processing and/or communication delays may prevent temporally accurate delivery of electrical stimulation where the device is configured to immediately deliver the electrical stimulation responsive to determining that electrical stimulation is to be delivered. In the example of theta stimulation, for a frequency of a theta wave of 2 Hz to 8 Hz, to deliver stimulation consistently at the peak of the wave may require delivery of stimulation in a window smaller than 30 ms. As variability in processing and communication may be in the hundreds of milliseconds, the ability to deliver electrical stimulation with temporal precision may be important in providing energy savings to the device and/or to optimizing therapy.

In accordance with one or more techniques of this disclosure, a device may execute a command to deliver electrical stimulation to a patient at a specific time. In some examples, the command may identify a count of a tick counter tied to a clock used by the device to deliver electrical stimulation. The clock may be a clock signal used by one or more processors that form and/or execute a stimulation engine of the device. In some examples, the device may increment the tick counter for every cycle of the clock. For instance, the device may increment the tick counter in response to rising edges or falling edges of the clock signal.

The device may deliver electrical stimulation to the patient based on the identified count of the tick counter. For instance, the device may deliver electrical stimulation at the identified count in response to determining that the identified count of the counter will occur after a current count of the counter. However, in some examples, the identified count of the counter may already have passed by the time the device receives the command that identifies the count. In some examples, even though the identified count of the counter has already passed, it may still be desirable to for the device to deliver electrical stimulation if it has not been too long since the identified count occurred. As such, in some examples, the device may deliver electrical stimulation at a current count of the counter in response to determining that the identified count of the counter has already occurred and a difference between the current count of the counter and the identified count of the counter satisfies a threshold count difference (i.e., is within a "tardy margin"). Similarly, in some examples, the device may refrain from delivering electrical stimulation based on the identified count in response to determining that the identified count of the counter has already occurred and a difference between the current count of the counter and the identified count of the counter does not satisfy a threshold count difference. In this way, the device may improve the temporal accuracy at which stimulation is delivered.

As discussed above, in some examples, the device may deliver electrical stimulation using closed-loop techniques. In such techniques, the device may deliver electrical stimulation to the patient based on sensed parameters of the patient. In some examples, the device may obtain representations of sensed electrical signals for the patient that are referenced to counts of the counter. The device may identify, based on the representations, a count of the counter at which stimulation is to be delivered to the patient. As the identification of the count is based on representations of sensed electrical signals for the patient that are referenced to counts of the counter, the device may better determine a future count to deliver stimulation to the patient. For instance, where it is desired to deliver stimulation synchronous with periodic activity electrical activity of the patient, the device may identify a future count predicted to coincide with a particular point or phase of the periodic activity (e.g., a peak of a theta wave, a though of the theta wave, etc.). In this way, the device may improve the temporal accuracy at which stimulation is delivered.

In some examples, the identification of the count at which stimulation is to be delivered may be entirely performed by the device that includes the stimulator. For instance, the device may obtain the representations of sensed electrical signals for the patient that are referenced to counts of the counter, identify the count based on the obtained representations, and deliver electrical stimulation based on the identified count. In some examples, where the identification of the count at which stimulation is to be delivered may be entirely performed by a device, the device may be considered to operate in an "embedded" mode.

In some examples, one or more other devices may participate in the identification of the count at which stimulation is to be delivered. For instance, the device that includes the stimulator may obtain the representations of sensed electrical signals for the patient that are referenced to counts of the counter, and output said representations for transmission (e.g., wired or wireless transmission) to another device. The other device may identify a count in the future at which stimulation is to be delivered based on the obtained representations, and transmit a command to the device that includes the stimulator that includes the identified count. The device that includes the stimulator may receive the command and deliver electrical stimulation based on the identified count. In some examples, where the identification of the count at which stimulation is to be delivered may entirely performed, at least in part, by devices other than the device that includes the stimulator, the system may be considered to operate in a "distributed" mode.

FIG. 1 is a conceptual diagram illustrating an example therapy system 10 that is configured to deliver therapy to patient 12 to manage a disorder of patient 12. Patient 12 ordinarily will be a human patient. In some cases, however, therapy system 10 may be applied to other mammalian or non-mammalian non-human patients. In the example shown in FIG. 1, therapy system 10 includes medical device programmer 14, implantable medical device (IMD) 16, lead extension 18, and one or more leads 20A and 20B (collectively "leads 20") with respective sets of electrodes 24, 26. IMD 16 includes a stimulation generator configured to generate and deliver electrical stimulation therapy to one or more regions of brain 28 of patient 12 via one or more electrodes 24, 26 of leads 20A and 20B, respectively.

In the example shown in FIG. 1, therapy system 10 may be referred to as a deep brain stimulation (DBS) system because IMD 16 is configured to deliver electrical stimulation therapy directly to tissue within brain 28, e.g., a tissue site under the dura mater of brain 28 or one or more branches or nodes, or a confluence of fiber tracks. In other examples, leads 20 may be positioned to deliver therapy to a surface of brain 28 (e.g., the cortical surface of brain 28). For example, in some examples, IMD 16 may provide cortical stimulation therapy to patient 12, e.g., by delivering electrical stimulation to one or more tissue sites in the cortex of brain 28. As another example, IMD 16 may provide vagal nerve stimulation (VNS) therapy to patient 12 by delivering electrical stimulation to one or more vagal nerve tissue sites.

DBS may be used to treat or manage various patient conditions, such as, but not limited to, seizure disorders (e.g., epilepsy), pain, migraine headaches, psychiatric disorders (e.g., major depressive disorder (MDD), bipolar disorder, anxiety disorders, post-traumatic stress disorder, dysthymic disorder, and obsessive compulsive disorder (OCD)), behavior disorders, mood disorders, memory disorders, mentation disorders, movement disorders (e.g., essential tremor or Parkinson's disease), Huntington's disease, Alzheimer's disease, or other neurological or psychiatric disorders and impairment of patient 12.

Therapy systems configured for treatment of other patient conditions via delivery of therapy to brain 28 or another suitable target therapy delivery site in patient 12 can also be used in accordance with the techniques disclosed herein. For example, in other applications of therapy system 10, the target therapy delivery site within patient 12 may be a location proximate to a spinal cord or sacral nerves (e.g., the S2, S3 or S4 sacral nerves) in patient 12 or any other suitable nerve, organ, muscle or muscle group in patient 12, which may be selected based on, for example, a patient condition. For example, therapy system 10 may be used to deliver electrical stimulation or a therapeutic agent to tissue proximate to a pudendal nerve, a perineal nerve or other areas of the nervous system, in which cases, leads 20 would be implanted and substantially fixed proximate to the respective nerve. As further examples, an electrical stimulation system may be positioned to deliver a stimulation to help manage peripheral neuropathy or post-operative pain mitigation, ilioinguinal nerve stimulation, intercostal nerve stimulation, gastric stimulation for the treatment of gastric mobility disorders and obesity, urinary dysfunction, fecal dysfunction, sexual dysfunction, muscle stimulation, for mitigation of other peripheral and localized pain (e.g., leg pain or back pain).

In the example shown in FIG. 1, IMD 16 may be implanted within a subcutaneous pocket in the pectoral region of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrodes on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. IMD 16 can be constructed of a biocompatible material that resists corrosion and degradation from bodily fluids. IMD 16 may comprise a hermetically sealed housing 34 to substantially enclose components, such as a processor, a therapy module, and memory.

In the example shown in FIG. 1, leads 20 are implanted within the right and left hemispheres, respectively, of brain 28 in order to deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere at multiple target tissue sites or IMD 16 may be coupled to a single lead that is implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 via any suitable technique, such as through respective burr holes in the skull of patient 12 or through a common burr hole in the cranium 32. Leads 20 may be placed at any location within brain 28 such that electrodes 24, 26 are capable of providing electrical stimulation to target therapy delivery sites within brain 28 during treatment. Different neurological or psychiatric disorders may be associated with activity in one or more of regions of brain 28, which may differ between patients. Accordingly, the target therapy delivery site for electrical stimulation therapy delivered by leads 20 may be selected based on the patient condition. For example, a suitable target therapy delivery site within brain 28 for controlling a movement disorder of patient 12 may include one or more of the pedunculopontine nucleus (PPN), thalamus, basal ganglia structures (e.g., globus pallidus, substantia nigra or subthalamic nucleus), zona inserta, fiber tracts, lenticular fasciculus (and branches thereof), ansa lenticularis, or the Field of Forel (thalamic fasciculus). The PPN may also be referred to as the pedunculopontine tegmental nucleus.

As another example, in the case of MDD, bipolar disorder, OCD, or other anxiety disorders, leads 20 may be implanted to deliver electrical stimulation to the anterior limb of the internal capsule of brain 28, and only the ventral portion of the anterior limb of the internal capsule (also referred to as a VC/VS), the subgenual component of the cingulate cortex (which may be referred to as CG25), anterior cingulate cortex Brodmann areas 32 and 24, various parts of the prefrontal cortex, including the dorsal lateral and medial pre-frontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the locus coeruleus, the dorsal raphe nucleus, ventral tegmentum, the substantia nigra, subthalamic nucleus, the inferior thalamic peduncle, the dorsal medial nucleus of the thalamus, the habenula, the bed nucleus of the stria terminalis, or any combination thereof.

As another example, in the case of a seizure disorder or Alzheimer's disease, for example, leads 20 may be implanted to deliver electrical stimulation to regions within the circuit of Papez, such as, e.g., one or more of the anterior thalamic nucleus, the internal capsule, the cingulate, the fornix, the mammillary bodies, the mammillothalamic tract (mammillothalamic fasciculus), or the hippocampus.

As another example, in the case of Parkinson's disease, for example, leads 20 may be implanted to deliver electrical stimulation to regions within the subthalamic nucleus (STN), either unilaterally or bilaterally. Target therapy delivery sites not located in brain 28 of patient 12 are also contemplated.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

In the examples shown in FIG. 1, electrodes 24, 26 of leads 20 are shown as ring electrodes. Ring electrodes may be relatively easy to program and may be capable of delivering an electrical field to any tissue adjacent to leads 20. In other examples, electrodes 24, 26 of leads 20 may have different configurations. For example, one or more of the electrodes 24, 26 of leads 20 may have a complex electrode array geometry that is capable of producing shaped electrical fields, including interleaved stimulation. An example of a complex electrode array geometry may include an array of electrodes positioned at different axial positions along the length of a lead, as well as at different angular positions about the periphery, e.g., circumference, of the lead. The complex electrode array geometry may include multiple electrodes (e.g., partial ring or segmented electrodes) around the perimeter of each lead 20, in addition to, or instead of, a ring electrode. In this manner, electrical stimulation may be directed to a specific direction from leads 20 to enhance therapy efficacy and reduce possible adverse side effects from stimulating a large volume of tissue. As a further example, the electrodes may be pad electrodes, which may be carried on a paddle lead or a cylindrical lead.

In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In other examples, leads 20 may have shapes other than elongated cylinders as shown in FIG. 1 with active or passive tip configurations. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs (also referred to herein as "set of stimulation parameter values"). A stimulation therapy program may define one or more electrical stimulation parameter values for therapy generated by a stimulation generator of IMD 16 and delivered from IMD 16 to a target therapy delivery site within patient 12 via one or more electrodes 24, 26. The electrical stimulation parameters may define an aspect of the electrical stimulation therapy, and may include, for example, voltage or current amplitude of an electrical stimulation signal, a charge level of an electrical stimulation, a frequency of the electrical stimulation signal, waveform shape, on/off cycling state (e.g., if cycling is "off," stimulation is always on, and if cycling is "on," stimulation is cycled on and off) and, in the case of electrical stimulation pulses, pulse rate, pulse width, and other appropriate parameters such as duration or duty cycle. In addition, if different electrodes are available for delivery of stimulation, a therapy parameter of a therapy program may be further characterized by an electrode combination, which may define selected electrodes 24, 26 and their respective polarities. In some examples, stimulation may be delivered using a continuous waveform and the stimulation parameters may define this waveform.

In addition to being configured to deliver therapy to manage a disorder of patient 12, therapy system 10 may be configured to sense bioelectrical brain signals or another physiological parameter of patient 12. For example, IMD 16 may include a sensing module that is configured to sense bioelectrical brain signals within one or more regions of brain 28 via a subset of electrodes 24, 26, another set of electrodes, or both. Accordingly, in some examples, electrodes 24, 26 may be used to deliver electrical stimulation from the therapy module to target sites within brain 28 as well as sense brain signals within brain 28. However, IMD 16 can also use a separate set of sensing electrodes to sense the bioelectrical brain signals. In some examples, the sensing module of IMD 16 may sense bioelectrical brain signals via one or more of the electrodes 24, 26 that are also used to deliver electrical stimulation to brain 28. In other examples, one or more of electrodes 24, 26 may be used to sense bioelectrical brain signals while one or more different electrodes 24, 26 may be used to deliver electrical stimulation.

External medical device programmer 14 is configured to wirelessly communicate with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. In addition, or instead, programmer 14 may be a patient programmer that allows patient 12 to select programs and/or view and modify therapy parameter values. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device, voice activation, or another input mechanism that allows the user to navigate through the user interface of programmer 14 and provide input. If programmer 14 includes buttons and a keypad, the buttons may be dedicated to performing a certain function, e.g., a power button, the buttons and the keypad may be soft keys that change in function depending upon the section of the user interface currently viewed by the user, or any combination thereof.

In other examples, programmer 14 may be a larger workstation or a separate application within another multifunction device, rather than a dedicated computing device. For example, the multi-function device may be a notebook computer, tablet computer, workstation, one or more servers, cellular phone, personal digital assistant, or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit programming information to IMD 16. Programming information may include, for example, hardware information, such as the type of leads 20, the arrangement of electrodes 24, 26 on leads 20, the position of leads 20 within brain 28, one or more therapy programs defining therapy parameter values, therapeutic windows for one or more electrodes 24, 26, and any other information that may be useful for programming into IMD 16. Programmer 14 may also be capable of completing functional tests (e.g., measuring the impedance of electrodes 24, 26 of leads 20).

The clinician may also generate and store therapy programs within IMD 16 with the aid of programmer 14. Programmer 14 may assist the clinician in the creation/identification of therapy programs by providing a system for identifying potentially beneficial therapy parameter values. For example, during a programming session, programmer 14 may automatically select a combination of electrodes for delivery to therapy to the patient. In some examples, at least some of the therapy programs may have the same electrode combination (but different values of at least one other therapy parameter) and these therapy programs may be organized into subsets, each subset having the same electrode combination. A processor of programmer 14 may select the most efficacious therapy program for each subset and display a list of the selected therapy programs. The clinician may select a therapy program from the list to provide therapy to patient 12 to address symptoms associated with the patient condition.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12.

Whether programmer 14 is configured for clinician or patient use, programmer 14 is configured to communicate with IMD 16 and, optionally, another computing device, via wireless communication. Programmer 14, for example, may communicate via wireless communication with IMD 16 using radio frequency (RF) and/or inductive telemetry techniques known in the art, which may comprise techniques for proximal, mid-range, or longer-range communication. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards, or memory sticks. Further, programmer 14 may communicate with IMD 16 and another programmer via remote telemetry techniques known in the art, communicating via a personal area network (PAN), a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

While DBS may successfully reduce symptoms of some neurological diseases, the stimulation may also cause unwanted side effects, also referred to herein as adverse effects. Side effects may include incontinence, tingling, loss of balance, paralysis, slurred speech, loss of memory, loss of inhibition, and many other neurological problems. Side effects may be mild to severe. DBS may cause one or more adverse effects by inadvertently providing electrical stimulation pulses to anatomical regions near the targeted anatomical region. These anatomical regions may be referred to as regions associated with adverse stimulation effects. For this reason, a clinician may program IMD 16 with a therapy program (or a plurality of therapy programs) that defines stimulation parameter values that balance effective therapy and minimize side effects.

With the aid of programmer 14 or another computing device, a clinician may select values for therapy parameters for therapy system 10, including an electrode combination. By selecting particular electrodes 24, 26 for delivering electrical stimulation therapy to patient 12, a clinician may modify the electrical stimulation therapy to target one or more particular regions of tissue (e.g., specific anatomical structures) within brain 28 and avoid other regions of tissue within brain 28. In addition, by selecting values for the other stimulation parameter values that define the electrical stimulation signal, e.g., the amplitude, pulse width, and pulse rate, the clinician may generate an efficacious therapy for patient 12 that is delivered via the selected electrode subset. Due to physiological diversity, condition differences, and inaccuracies in lead placement, the parameter values may vary between patients.

During a programming session, the clinician may determine one or more therapy programs that may provide effective therapy to patient 12. Patient 12 may provide feedback to the clinician as to the efficacy of the specific program being evaluated, which may include information regarding adverse effects of delivery of therapy according to the specific program. In some examples, the patient feedback may be used to determine a clinical rating scale score. Once the clinician has identified one or more programs that may be beneficial to patient 12, patient 12 may continue the evaluation process and determine which program best alleviates the condition of patient 12 or otherwise provides efficacious therapy to patient 12. Programmer 14 may assist the clinician in the creation/identification of therapy programs by providing a methodical system of identifying potentially beneficial therapy parameters.

IMD 16 may be configured to deliver electrical stimulation based on a clock. For instance, a stimulation engine of IMD 16 (e.g., one or more processors and/or one or more stimulation generators of IMD 16) may perform one or more operations based on a clock signal.

In accordance with one or more techniques of this disclosure, and as discussed in further detail below, in some examples, a device (e.g., IMD 16, programmer 14, and/or another computing device) may be configured to automatically identify a count of a counter incremented based on the clock used by IMD 16 at which stimulation is to be delivered to the patient. For instance, the device may issue a command to stimulate at a particular count of the counter. As one example, the stimulation engine of IMD 16 may generate the command. As another example, programmer 14 may transmit the command to IMD 16.

IMD 16 may execute the command to deliver stimulation to the patient. For instance, IMD 16 may deliver electrical stimulation at the identified count in response to determining that the identified count of the counter will occur after a current count of the counter. However, in some examples, the identified count of the counter may already have passed by the time IMD 16 receives the command that identifies the count. In some examples, even though the identified count of the counter has already passed, it may still be desirable to for IMD 16 to deliver electrical stimulation if it has not been too long since the identified count occurred. As such, in some examples, IMD 16 may deliver electrical stimulation at a current count of the counter in response to determining that the identified count of the counter has already occurred and a difference between the current count of the counter and the identified count of the counter satisfies a threshold count difference. The difference between the current count of the counter and the identified count of the counter may satisfy the satisfies a threshold count difference where the difference between the current count of the counter and the identified count of the counter is less than or equal to the threshold count difference. In some examples, IMD 16 may refrain from delivering electrical stimulation based on the identified count in response to determining that the identified count of the counter has already occurred and a difference between the current count of the counter and the identified count of the counter does not satisfy a threshold count difference. In this way, IMD 16 may improve the temporal accuracy at which stimulation is delivered.

Figure 2:
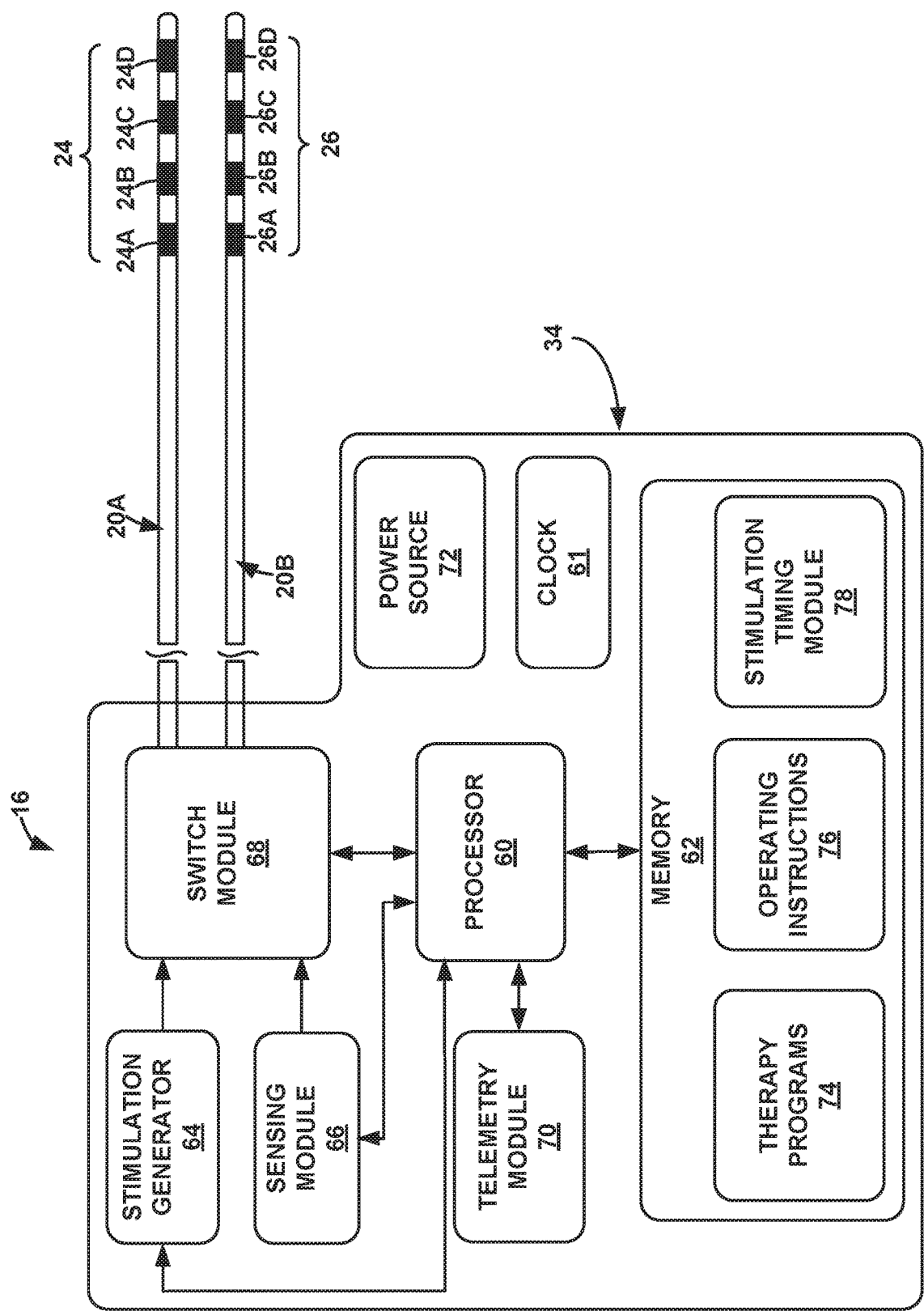
FIG. 2 is functional block diagram illustrating components of an example medical device.

FIG. 2 is functional block diagram illustrating components of an example IMD 16. In the example shown in FIG. 2, IMD 16 includes processor 60, clock 61, memory 62, stimulation generator 64, sensing module 66, switch module 68, telemetry module 70, and power source 72. Memory 62, as well as other memories described herein, may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 16 to perform various functions described herein.

In the example shown in FIG. 2, memory 62 may store therapy programs 74, operating instructions 76, and stimulation timing module 78, e.g., in separate memories within memory 62 or separate areas within memory 62. Each stored therapy program 74 defines a particular program of therapy in terms of respective values for electrical stimulation parameters, such as an electrode combination, current or voltage amplitude, and, if stimulation generator 64 generates and delivers stimulation pulses, the therapy programs may define values for a pulse width, and pulse rate of a stimulation signal. Each stored therapy program 74 may also be referred to as a set of stimulation parameter values. Operating instructions 76 guide general operation of IMD 16 under control of processor 60, and may include instructions for monitoring brain signals within one or more brain regions via electrodes 24, 26 and delivering electrical stimulation therapy to patient 12. As discussed in further detail below and in accordance with one or more techniques of this disclosure, in some examples, memory 62 may store stimulation timing module 78, which may include instructions that are executable by processor 60 to enable delivery of electrical stimulation at a precise time.

Stimulation generator 64, under the control of processor 60, generates stimulation signals for delivery to patient 12 via selected combinations of electrodes 24, 26. In some examples, stimulation generator 64 generates and delivers stimulation signals to one or more target regions of brain 28 (FIG. 1), via a selected combination of electrodes 24, 26, based on one or more stored therapy programs 74. The target tissue sites within brain 28 for stimulation signals or other types of therapy and stimulation parameter values may depend on the patient condition for which therapy system 10 is implemented to manage. While stimulation pulses are described, stimulation signals may be of any form, such as continuous-time signals (e.g., sine waves) or the like.

Clock 61 may output a clock signal to one or more components of IMD 16. For instance, clock 61 may output a clock signal to processor 60 and/or stimulation generator 64. In some examples, clock 61 may include an oscillator or any other clock generator.

The processors described in this disclosure, including processor 60, may include one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Processor 60 may be configured to perform one or more operations based on a clock signal, such as a clock signal received from clock 61. Processor 60 is configured to control stimulation generator 64 according to therapy programs 74 stored by memory 62 to apply particular stimulation parameter values specified by one or more programs, such as amplitude, pulse width, and pulse rate.

In the example shown in FIG. 2, the set of electrodes 24 of lead 20A includes electrodes 24A-24D, and the set of electrodes 26 of lead 20B includes electrodes 26A-26D. Processor 60 may control switch module 68 to apply the stimulation signals generated by stimulation generator 64 to a selected combination of electrodes 24 and/or electrodes 26. In particular, switch module 68 may couple stimulation signals to selected conductors within leads 20, which, in turn, deliver the stimulation signals across selected electrodes 24 and/or electrodes 26. Switch module 68 may be a switch array, switch matrix, multiplexer, or any other type of switching module configured to selectively couple stimulation energy to selected electrodes 24 and/or electrodes 26 and to selectively sense bioelectrical brain signals with selected electrodes 24 and/or electrodes 26. Hence, stimulation generator 64 is coupled to electrodes 24 and/or electrodes 26 via switch module 68 and conductors within leads 20. In some examples, however, IMD 16 does not include switch module 68. For instance, in some examples, IMD 16 may include individual voltage or current sources coupled to each electrode (i.e., a separate voltage and/or current source for each of electrodes 24 and/or electrodes 26).

As discussed above, processor 60 may control switch module 68 to apply the stimulation signals generated by stimulation generator 64 to a selected combination of electrodes 24 and/or electrodes 26. In some examples, the selected combination of electrodes 24 and/or electrodes 26 may be unipolar. For instance, a unipolar selected combination may include one contact of either electrodes 24 or electrodes 26 in combination with an electrode on the housing of IMD 16 (i.e., case or can), where one is an anode and the other is a cathode. In some examples, the selected combination of electrodes 24 and/or electrodes 26 may be bipolar. As one example, a bipolar selected combination may include two contacts from electrodes 24, where one is an anode and the other is a cathode. As another example, a bipolar selected combination may include two electrodes from contacts 26, where one is an anode and the other is a cathode. As another example, a bipolar selected combination may include an electrode from electrodes 24 and an electrode from electrodes 26, where one is an anode and the other is a cathode. In some examples, the selected combination of electrodes 24 and/or electrodes 26 may be multi-polar. As one example, a multipolar selected combination may include multiple anodes and/or multiple cathodes selected from electrodes 24. As another example, a multipolar selected combination may include multiple anodes and/or multiple cathodes selected from electrodes 26. As one example, a multipolar selected combination may include multiple anodes and/or multiple cathodes selected from electrodes 24 and electrodes 26.

Stimulation generator 64 may be a single channel or multi-channel stimulation generator. In particular, stimulation generator 64 may be capable of delivering a single stimulation pulse, multiple stimulation pulses or continuous signal at a given time via a single electrode combination or multiple stimulation pulses at a given time via multiple electrode combinations. In some examples, however, stimulation generator 64 and switch module 68 may be configured to deliver multiple channels on a time-interleaved basis. For example, switch module 68 may serve to time divide the output of stimulation generator 64 across different electrode combinations at different times to deliver multiple programs or channels of stimulation energy to patient 12. Stimulation generator 64 may be configured to perform one or more operations based on a clock signal, such as a clock signal received from clock 61.

Sensing module 66, under the control of processor 60, is configured to sense bioelectrical brain signals of patient 12 via a selected subset of electrodes 24 and/or electrodes 26 or with one or more electrodes 24 and/or electrodes 26 and at least a portion of a conductive outer housing 34 of IMD 16, an electrode on an outer housing of IMD 16 or another reference. Processor 60 may control switch module 68 to electrically connect sensing module 66 to selected electrodes 24 and/or electrodes 26. In this way, sensing module 66 may selectively sense bioelectrical brain signals with different combinations of electrodes 24 and/or electrodes 26 (and/or a reference other than an electrode of electrodes 24 and/or electrodes 26).

Although sensing module 66 is incorporated into a common housing 34 with stimulation generator 64 and processor 60 in FIG. 2, in other examples, sensing module 66 is in a separate outer housing from outer housing 34 of IMD 16 and communicates with processor 60 via wired or wireless communication techniques.

Telemetry module 70 is configured to support wireless communication between IMD 16 and an external programmer 14 or another computing device under the control of processor 60. Processor 60 of IMD 16 may receive, as updates to programs, values for various stimulation parameters such as amplitude and electrode combination, from programmer 14 via telemetry module 70. The updates to the therapy programs may be stored within therapy programs 74 portion of memory 62. Telemetry module 70 in IMD 16, as well as telemetry modules in other devices and systems described herein, such as programmer 14, may accomplish communication by RF communication techniques. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14. In some examples, the latency of the link between telemetry module 70 and programmer 14 may be variable. For instance, the amount of time to transfer a particular piece of data between telemetry module 70 and programmer 14 may change over time (i.e., may not be a consistent fixed value).

Power source 72 delivers operating power to various components of IMD 16. Power source 72 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

In accordance with one or more techniques of this disclosure, stimulation timing module 78 may be executable by processors 60 to enable IMD 16 to deliver electrical stimulation at a precise time. For instance, stimulation timing module 78 may identify a count of a counter at which stimulation is to be delivered to the patient. In some examples, the counter may be incremented based on (i.e., tied to) clock 61.

As discussed above, in some examples, IMD 16 may deliver electrical stimulation using closed-loop techniques. In such techniques, IMD 16 may deliver electrical stimulation to the patient based on sensed parameters of the patient, such as representations of sensed electrical signals obtained by sensing module 66. In some examples, the representations of sensed electrical signals for the patient may be referenced to counts of the counter. For instance, samples of electrical signals for the patient measured at a particular time may be tagged with a count of the counter at the particular time.

Stimulation timing module 78 may identify, based on the representations, a count of the counter at which stimulation is to be delivered to the patient. As the identification of the count is based on representations of sensed electrical signals for the patient that are referenced to counts of the counter, stimulation timing module 78 may better determine a future count to deliver stimulation to the patient. For instance, stimulation timing module 78 may enable delivery of electrical stimulation to a patent in synchronous with functions such as peak tremor from an external source or theta rhythms from internal brain signals. For one example, stimulation timing module 78 may analyze representations of sensed electrical signals for a patient to predict a count of the counter that will coincide with a peak of a theta wave of the patient. Stimulation timing module 78 may generate a command to deliver stimulation at the identified tick count. In some examples, the command may further identify a therapy program of therapy programs 74 to use to deliver the electrical stimulation (i.e., a therapy program that specifies an electrode combination, current or voltage amplitude, etc.).

In some examples, amount of time taken by stimulation timing module 78 to identify the count may be variable. For instance, the amount of time to analyze sensed electrical signals and identify a count at which stimulation is to be delivered may change over time (i.e., may not be a consistent fixed value).

IMD 16 may execute the instruction. For instance, stimulation timing module 78 may cause stimulation generator 64 deliver electrical stimulation at the identified count in response to determining that the identified count of the counter will occur after a current count of the counter. However, in some examples, the identified count of the counter may already have passed by the time the device receives the command that identifies the count. In some examples, even though the identified count of the counter has already passed, it may still be desirable to for IMD 16 to deliver electrical stimulation if it has not been too long since the identified count occurred. As such, in some examples, stimulation timing module 78 may cause stimulation generator 64 to deliver electrical stimulation at a current count of the counter in response to determining that the identified count of the counter has already occurred and a difference between the current count of the counter and the identified count of the counter satisfies a threshold count difference (i.e., is within a "tardy margin"). Similarly, in some examples, stimulation timing module 78 may refrain from causing stimulation generator 64 to deliver electrical stimulation based on the identified count in response to determining that the identified count of the counter has already occurred and a difference between the current count of the counter and the identified count of the counter does not satisfy a threshold count difference. In this way, stimulation timing module 78 may improve the temporal accuracy at which stimulation is delivered.

In some examples, one or more of the operations performed by stimulation timing module 78 of IMD 16 may be distributed across one or more other devices. For instance, as described below with reference to FIG. 3, an external device (e.g., programmer 14) may identify the count, generate the command, and transmit the command to IMD 16.

Figure 3:
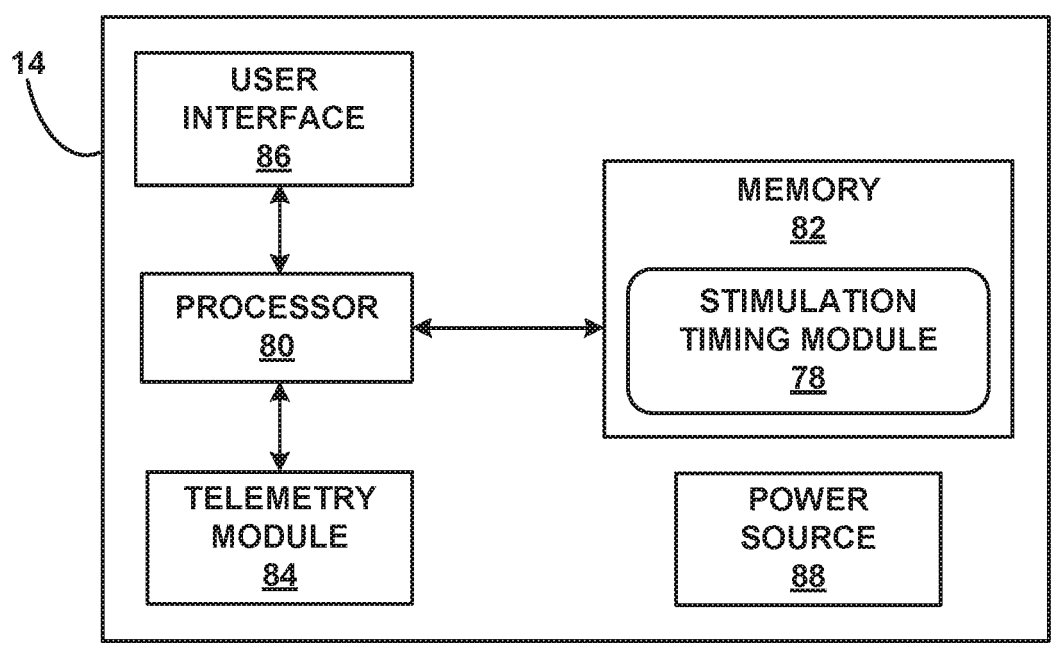
FIG. 3 is a functional block diagram illustrating components of an example medical device programmer.

FIG. 3 is a functional block diagram illustrating components of an example medical device programmer 14 (FIG. 1). Programmer 14 includes processor 80, memory 82, telemetry module 84, user interface 86, and power source 88. Processor 80 controls user interface 86 and telemetry module 84, and stores and retrieves information and instructions to and from memory 82. Programmer 14 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80.

A user, such as a clinician or patient 12, may interact with programmer 14 through user interface 86. User interface 86 includes a display (not shown), such as a LCD or LED display or other type of screen, with which processor 80 may present information related to the therapy (e.g., electrodes and associated therapeutic windows). In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processor 80 of programmer 14 and provide input. In other examples, user interface 86 also includes audio circuitry for providing audible notifications, instructions or other sounds to patient 12, receiving voice commands from patient 12, or both.

Memory 82 may include instructions for operating user interface 86 and telemetry module 84, and for managing power source 88. In the example shown in FIG. 3, memory 82 also stores counter module 78.

In some examples, patient 12, a clinician or another user may interact with user interface 86 of programmer 14 in other ways to manually select therapy programs, generate new therapy programs, modify therapy programs, transmit the new programs to IMD 16, or any combination thereof.

Memory 82 may include any volatile or nonvolatile memory, such as RAM, ROM, EEPROM or flash memory.

Memory 82 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 84. Accordingly, telemetry module 84 may be similar to the telemetry module contained within IMD 16. In other examples, programmer 14 may be capable of infrared communication or direct communication through a wired connection. In this manner, other external devices may be capable of communicating with programmer 14 without needing to establish a secure wireless connection.

Power source 88 is configured to deliver operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate.

While various information is illustrated and described as stored in memory 82 of programmer 14, it will be understood that some or all of this information could alternatively or additionally be stored within memory 62 of IMD 16. Moreover, at least some of the functionality ascribed to processor 80 of programmer 14 may instead or additionally be ascribed to processor 60 of IMD 16 as discussed below (and vice versa). For instance, as discussed above, stimulation timing module 78 of programmer 14 may identify a count of the counter maintained by IMD 16 at which stimulation is to be delivered. Stimulation timing module 78 may generate and cause telemetry module 84 to transmit, to telemetry module 70 of IMD 16, a command that indicates the identified count at which stimulation is to be delivered.

In some examples, stimulation timing module 78 of programmer 14 may identify the count based on sensed electrical signals for the patient. For instance, telemetry module 70 of IMD 16 may transmit, to telemetry module 84 of programmer 14, one or more representations of sensed electrical signals for the patient that are referenced to counts of a counter tied to a clock used by IMD 16 to deliver the electrical stimulation to the patient.

Figure 4B:
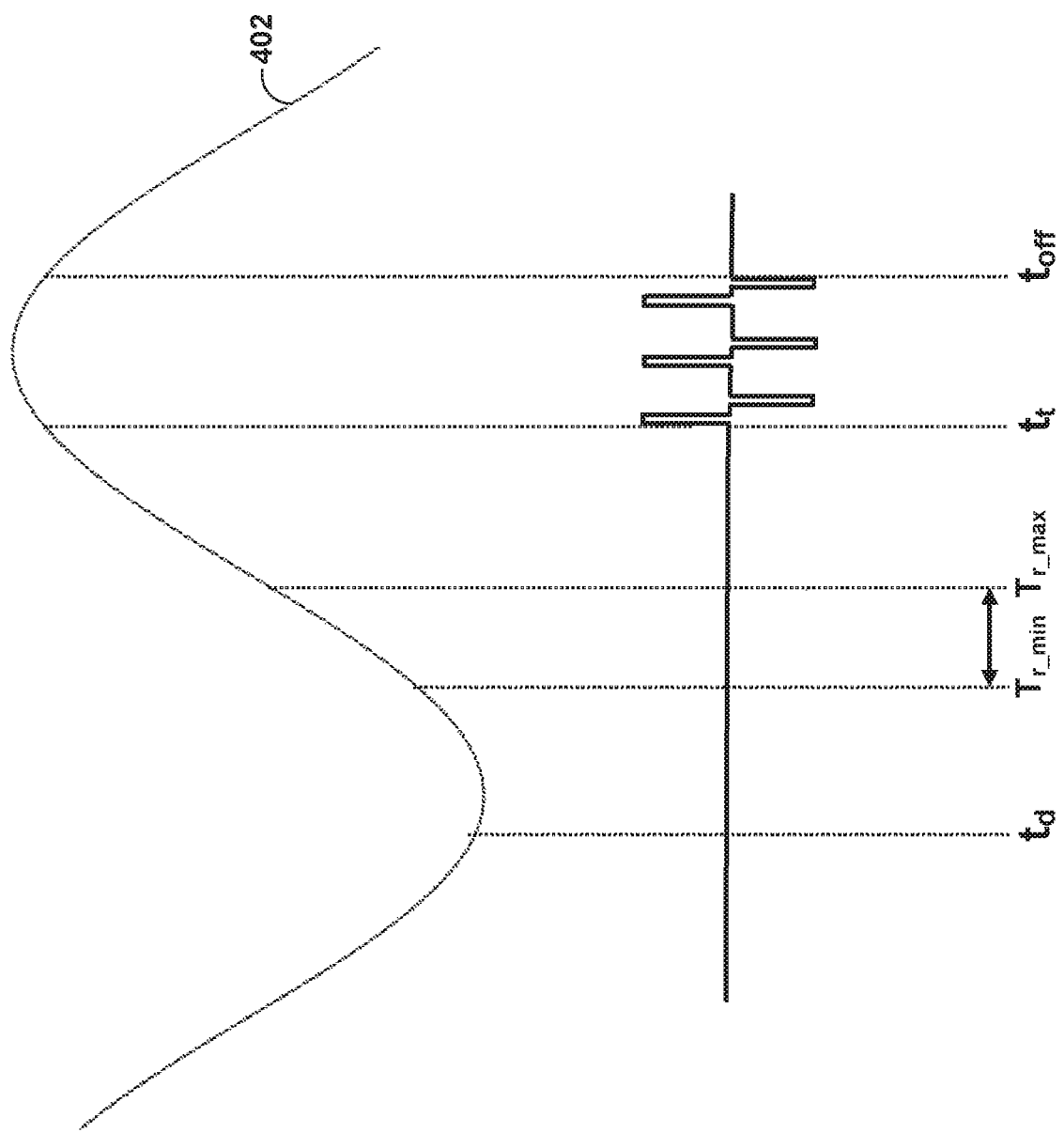

FIGS. 4A and 4B are graphs illustrating example delivery of electrical stimulation therapy to a patient, in accordance with one or more techniques of this disclosure. FIG. 4B may represent a magnified portion of FIG. 4A. For instance, FIG. 4B may represent the portion of FIG. 4A within region 400. Plot 402 of FIGS. 4A and 4B may represent a biomarker of a patient, such as sensed and/or processed electrical signals of a patient. In this example of FIGS. 4A and 4B, the desired stimulation may be biphasic pulses centered at the peak phase of the biomarker.

In accordance with one or more techniques of this disclosure, the biomarker of the patient may be analyzed and a decision to deliver stimulation at time $t_r$ (target time) may occur at time $t_d$ (decision time). The command to deliver the stimulation at time $t_r$ may be transmitted to the stimulating device (e.g., IMD 16) at time $t_t$.

The command may be received by the stimulating device between time $t_{r\_min}$ and $t_{r\_max}$. As discussed above, the amount of time taken to transfer the command is dependent upon the communication channel and is a distribution, not a single consistent time. Upon receipt of the command, the stimulating device may schedule the stimulation for $t_r$.

At time $t_r$, the stimulating device may begin to deliver stimulation. At time $t_{off}$, the stimulating device may complete the delivery of stimulation. Stimulation could be a set number of pulses at a set rate, or an off time could be scheduled.

Figure 5:
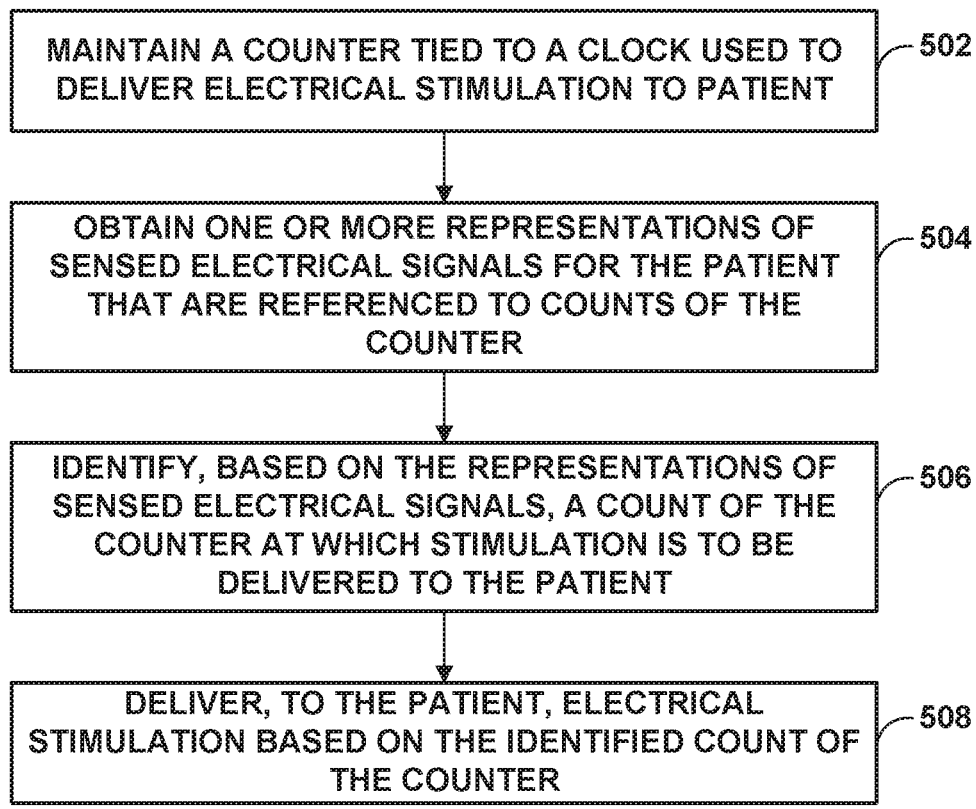
FIG. 5 is a flow diagram illustrating an example technique for delivering electrical stimulation to a patient at a precise time, in accordance with one or more techniques of this disclosure.

FIG. 5 is a flow diagram illustrating an example technique for delivering electrical stimulation to a patient at a precise time, in accordance with one or more techniques of this disclosure. For purposes of explanation, the technique of FIG. 5 will be described with respect to processor 60 of IMD 16. However, processors other than processor 60 may perform some or all of the technique of FIG. 5.

IMB 16 may maintain a counter tied to a clock used by IMD 16 to deliver the electrical stimulation to a patient (502). The clock may be a clock signal used by processor 60 and/or stimulation generator 64 of IMD 16 that form and/or execute a stimulation engine of the IMB 16. In some examples, processor 60 may increment the counter, which may be referred to as a tick counter, for every cycle of the clock. For instance, processor 60 may increment the tick counter in response to rising edges or falling edges of the clock signal.

IMD 16 may obtain one or more representations of sensed electrical signals for the patient that are referenced to counts of the counter (504). For instance, sensing module 66 of IMD 16 may measure bioelectrical brain signals of the patient via a selected subset of electrodes 24 and/or electrodes 26 or with one or more electrodes 24 and/or electrodes 26 and at least a portion of a conductive outer housing 34 of IMD 16, an electrode on an outer housing of IMD 16 or another reference. Processor 60 or sensing module 66 may time stamp the measurements with the value of the counter at the time the measurements were performed. As such, the representations of sensed electrical signals may be considered to be referenced to counts of the counter.

IMD 16 may identify, based on the one or more representations of the sensed electrical signals for the patient, a count of the counter at which stimulation is to be delivered to the patient (506). For instance, processor 60 may execute stimulation timing module 78 to determine a future count to deliver stimulation to the patient. For instance, stimulation timing module 78 may enable delivery of electrical stimulation to a patent in synchronous with functions such as peak tremor from an external source or theta rhythms from internal brain signals. For one example, stimulation timing module 78 may analyze the representations of sensed electrical signals for the patient to predict a count of the counter that will coincide with a peak of a theta wave of the patient. Stimulation timing module 78 may generate a command to deliver stimulation at the identified tick count. In some examples, the command may further identify a therapy program of therapy programs 74 to use to deliver the electrical stimulation (e.g., a therapy program that specifies an electrode combination, current or voltage amplitude, etc.).

In some examples, one or more other devices may participate in the identification of the count at which stimulation is to be delivered. For instance, IMD 16 obtain the representations of sensed electrical signals for the patient that are referenced to counts of the counter, and output said representations for transmission (e.g., wired or wireless transmission) to another device, such as programmer 15. The other device may identify a count in the future at which stimulation is to be delivered based on the obtained representations, and transmit a command to IMD 16 that includes the identified count. IMD 16 may receive the command and deliver electrical stimulation based on the identified count. As such, in some examples, IMD 16 may identify the count of the counter at which stimulation is to be delivered to the patient by receiving a command from another device, such as programmer 15.

IMD 16 may deliver, to the patient, electrical stimulation based on the identified count of the counter (508). As one example, stimulation timing module 78 may cause stimulation generator 64 deliver the electrical stimulation to the patient at the identified count. As another example, stimulation timing module 78 may cause stimulation generator 64 deliver the electrical stimulation to the patient at a count determined based on the identified count (e.g., N counts before the identified count, M counts after the identified count, etc.).

Figure 6:
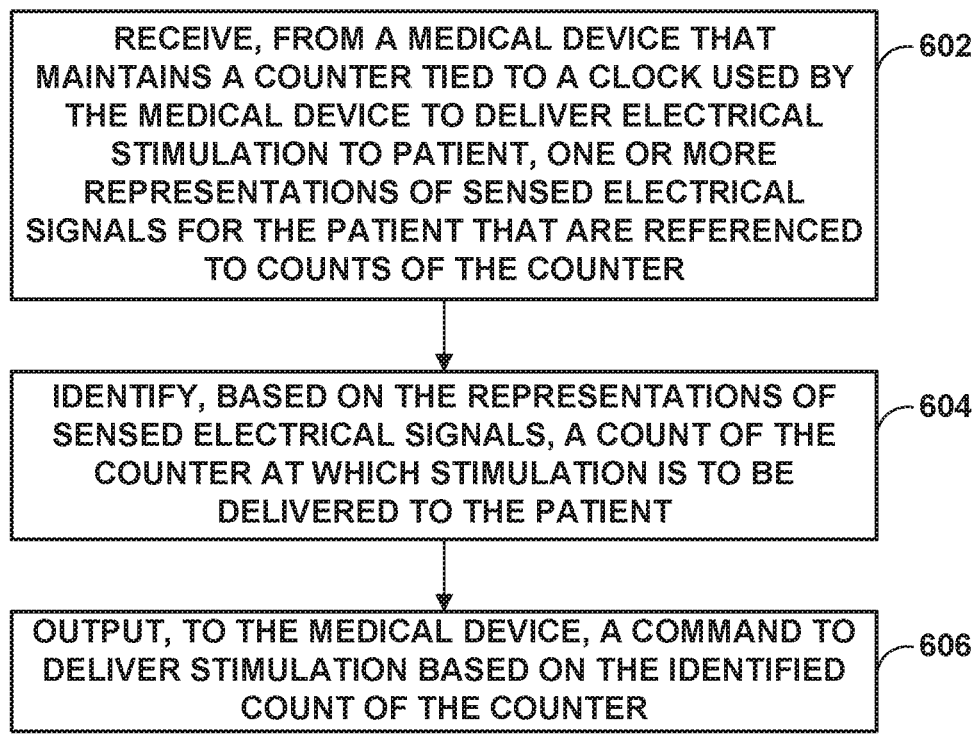
FIG. 6 is a flow diagram illustrating an example technique for controlling the delivery of electrical stimulation to a patient at a precise time, in accordance with one or more techniques of this disclosure.

FIG. 6 is a flow diagram illustrating an example technique for controlling the delivery of electrical stimulation to a patient at a precise time, in accordance with one or more techniques of this disclosure. For purposes of explanation, the technique of FIG. 6 will be described with respect to processor 80 of programmer 14. However, processors other than processor 80 may perform some or all of the technique of FIG. 6.

Programmer 14 may receive, from a medical device that maintains a counter tied to a clock used by the medical device to deliver the electrical stimulation to a patient, one or more representations of sensed electrical signals for the patient that are referenced to counts of the counter (602). For instance, processor 80 of programmer 14 may receive, from IMD 16 and via telemetry module 84 of programmer 14, the representations of sensed electrical signals that are referenced (e.g., tagged, stamped, etc.) to counts of the counter.

Programmer 14 may identify, based the representations of sensed electrical signals for the patient, a count of the counter at which stimulation is to be delivered to the patient (604). For instance, processor 80 may execute stimulation timing module 78 to determine a future count to deliver stimulation to the patient. For instance, stimulation timing module 78 may enable delivery of electrical stimulation to a patent in synchronous with functions such as peak tremor from an external source or theta rhythms from internal brain signals. For one example, stimulation timing module 78 may analyze the representations of sensed electrical signals for the patient to predict a count of the counter that will coincide with a peak of a theta wave of the patient. Stimulation timing module 78 may generate a command to deliver stimulation at the identified tick count. In some examples, the command may further identify a therapy program to use to deliver the electrical stimulation (i.e., a therapy program that specifies an electrode combination, current or voltage amplitude, etc.).

Programmer 14 may output, to the medical device, a command to deliver stimulation based on the identified count of the counter (606). For instance, processor 80 may cause telemetry module 84 to transmit, to the medical device, the command to deliver stimulation based on the identified count of the counter. As one example, telemetry module 84 transmit a command that causes the medical device to deliver the electrical stimulation to the patient at the identified count. As another example, telemetry module 84 transmit a command that causes the medical device to deliver the electrical stimulation to the patient at a count determined based on the identified count (e.g., N counts before the identified count, M counts after the identified count, etc.).

While the techniques described above are primarily described as being performed by processor 60 of IMD 16 or processor 80 of programmer 14, in other examples, one or more other processors may perform any part of the techniques described herein alone or in addition to processor 60 or processor 80. Thus, reference to "a processor" may refer to "one or more processors." Likewise, "one or more processors" may refer to a single processor or multiple processors in different examples.

The techniques described in this disclosure, including those attributed to IMD 16, programmer 14, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored, as one or more instructions or code, on a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structures or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples of the disclosure have been described. These and other embodiments are within the scope of the following claims.

What is claimed is:

1. A method for controlling delivery of electrical stimulation therapy, the method comprising:
maintaining, by one or more processors of a medical device configured to deliver electrical stimulation to a patient, a counter tied to a clock used by the medical device to deliver the electrical stimulation to the patient;

obtaining, by the one or more processors, one or more representations of sensed electrical signals for the patient that are referenced to counts of the counter;

identifying, by the one or more processors and based on the one or more representations of the sensed electrical signals for the patient, a count of the counter at which stimulation is to be delivered to the patient; and delivering, by the medical device and to the patient, electrical stimulation based on the identified count of the counter.

2. The method of claim 1, further comprising:

outputting, by the one or more processors of the medical device and for transmission to another device, the representations of sensed electrical signals for the patient that are referenced to counts of the counter, wherein identifying the count of the counter at which stimulation is to be delivered to the patient comprises:

receiving, by the one or more processors and from the other device, the identified count of the counter at which stimulation is to be delivered to the patient.

3. The method of claim 1, wherein delivering electrical stimulation based on the identified count of the counter comprises:

delivering electrical stimulation at the identified count of the counter in response to determining that the identified count of the counter will occur after a current count of the counter.

4. The method of claim 1, wherein delivering electrical stimulation based on the identified count of the counter comprises:

delivering electrical stimulation at a current count of the counter in response to determining that the identified count of the counter has already occurred and a difference between the current count of the counter and the identified count of the counter satisfies a threshold count difference.

5. The method of claim 1, wherein delivering electrical stimulation based on the identified count of the counter comprises:

refraining from delivering electrical stimulation based on the identified count in response to determining that the identified count of the counter has already occurred and a difference between the current count of the counter and the identified count of the counter does not satisfy a threshold count difference.

6. The method of claim 1, wherein identifying the count comprises:

identifying, by the one or more processors, a count of the counter predicted to coincide with an activity of the patient.

7. The method of claim 6, wherein the activity of the patient comprises a peak in a theta wave of a brain of the patient.

8. The method of claim 6, wherein the activity of the patient comprises a point in a periodic signal in electrical signals of the patient.

9. The method of claim 6, wherein the activity of the patient comprises a phase in a periodic signal in electrical signals of the patient.

10. A medical device comprising:

a memory configured to store a representation of sensed electrical signals for a patient; and one or more processors configured to:

maintain a counter tied to a clock used by the medical device to deliver electrical stimulation to a patient;

obtain one or more representations of sensed electrical signals for the patient that are referenced to counts of the counter;

identify, based on the one or more representations of the sensed electrical signals for the patient, a count of the counter at which stimulation is to be delivered to the patient; and deliver, to the patient, electrical stimulation based on the identified count of the counter.

11. The medical device of claim 10, further comprising:

a telemetry module configured to transmit, to another device, the representations of sensed electrical signals for the patient that are referenced to counts of the counter, wherein, to identify the count of the counter at which stimulation is to be delivered to the patient, the one or more processors are configured to:

receive, via the telemetry module and from the other device, the identified count of the counter at which stimulation is to be delivered to the patient.

12. The medical device of claim 10, wherein, to deliver electrical stimulation based on the identified count of the counter, the one or more processors are configured to:

deliver electrical stimulation at the identified count of the counter in response to determining that the identified count of the counter will occur after a current count of the counter.

13. The medical device of claim 10, wherein, to deliver electrical stimulation based on the identified count of the counter, the one or more processors are configured to:

deliver electrical stimulation at a current count of the counter in response to determining that the identified count of the counter has already occurred and a difference between the current count of the counter and the identified count of the counter satisfies a threshold count difference.

14. The medical device of claim 10, wherein, to deliver electrical stimulation based on the identified count of the counter, the one or more processors are configured to:

refrain from delivering electrical stimulation based on the identified count in response to determining that the identified count of the counter has already occurred and a difference between the current count of the counter and the identified count of the counter does not satisfy a threshold count difference.

15. The medical device of claim 10, wherein, to identify the count, the one or more processors are configured to:

identify a count of the counter predicted to coincide with an activity of the patient.

16. The medical device of claim 15, wherein the activity of the patient comprises one or more of:

a peak in a theta wave of a brain of the patient;

a point in a periodic signal in electrical signals of the patient; or a phase in a periodic signal in electrical signals of the patient.

17. A method for controlling delivery of electrical stimulation therapy, the method comprising:

receiving, by a telemetry module of a device and from a medical device that maintains a counter tied to a clock used by the medical device to deliver the electrical stimulation to a patient, one or more representations of sensed electrical signals for the patient that are referenced to counts of the counter;

identify, by one or more processors of the device and based the representations of sensed electrical signals for the patient, a count of the counter at which stimulation is to be delivered to the patient; and output, by the telemetry module and to the medical device, a command to deliver stimulation based on the identified count of the counter.

18. The method of claim 17, wherein identifying the count comprises:

identifying, by the one or more processors, a count of the counter predicted to coincide with an activity of the patient.

19. The method of claim 18, wherein the activity of the patient comprises a peak in a theta wave of a brain of the patient.

20. The method of claim 18, wherein the activity of the patient comprises a point in a periodic signal in electrical signals of the patient.

21. The method of claim 18, wherein the activity of the patient comprises a phase in a periodic signal in electrical signals of the patient.

22. A medical device programmer comprising:

a telemetry module configured to communicate with a medical device that maintains a counter tied to a clock used by the medical device to deliver the electrical stimulation to a patient; and one or more processors configured to:

receive, via the telemetry module from the medical device, one or more representations of sensed electrical signals for the patient that are referenced to counts of the counter;

identify, based the representations of sensed electrical signals for the patient, a count of the counter at which stimulation is to be delivered to the patient; and output, via the telemetry module and to the medical device, a command to deliver stimulation based on the identified count of the counter.

23. The medical device of claim 22, wherein identifying the count comprises:

identifying, by the one or more processors, a count of the counter predicted to coincide with an activity of the patient.

24. The medical device of claim 23, wherein the activity of the patient comprises one or more of:

a peak in a theta wave of a brain of the patient;

a point in a periodic signal in electrical signals of the patient; or a phase in a periodic signal in electrical signals of the patient.

25. A computer-readable storage medium storing instructions that, when executed, cause one or more processors of a medical device programmer to:

receive, via a telemetry module of the medical device programmer and from a medical device that maintains a counter tied to a clock used by the medical device to deliver the electrical stimulation to a patient, one or more representations of sensed electrical signals for the patient that are referenced to counts of the counter;

identify, based the representations of sensed electrical signals for the patient, a count of the counter at which stimulation is to be delivered to the patient; and output, via the telemetry module and to the medical device, a command to deliver stimulation based on the identified count of the counter.

26. A system comprising:

a medical device configured to maintain a counter tied to a clock used by the medical device to deliver the electrical stimulation to the patient; and one or more processors configured to identify, based on one or more representations of sensed electrical signals for the patient that are referenced to counts of the counter, a count of the counter at which stimulation is to be delivered to the patient, wherein the medical device is configured to deliver stimulation to the patient based on the identified count.

* * * * *